(12) United States Patent
Yamada (10) Patent No.: US 11,911,130 B2
(45) Date of Patent: Feb. 27, 2024

(54) BRAIN FUNCTION MEASUREMENT DEVICE, BRAIN FUNCTION MEASUREMENT METHOD, AND PROBE

(71) Applicant: NATIONAL INSTITUTE OF ADVANCED INDUSTRIAL SCIENCE AND TECHNOLOGY, Tokyo (JP)

(72) Inventor: Toru Yamada, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 579 days.

(21) Appl. No.: 17/256,081

(22) PCT Filed: Dec. 20, 2019

(86) PCT No.: PCT/JP2019/050040
§ 371 (c)(1),
(2) Date: Dec. 24, 2020

(87) PCT Pub. No.: WO2020/174842
PCT Pub. Date: Sep. 3, 2020

(65) Prior Publication Data
US 2021/0145286 A1    May 20, 2021

(30) Foreign Application Priority Data
Feb. 27, 2019    (JP) .................. 2019-034300

(51) Int. Cl.
*A61B 5/00* (2006.01)
(52) U.S. Cl.
CPC .......... *A61B 5/0075* (2013.01); *A61B 5/4064* (2013.01); *A61B 2562/0233* (2013.01); *A61B 2562/223* (2013.01)

(58) Field of Classification Search
CPC ............... A61B 5/0075; A61B 5/4064; A61B 2562/0233
See application file for complete search history.

(56) References Cited

U.S. PATENT DOCUMENTS 5,596,992 A * 1/1997 Haaland ............... A61B 5/7264
250/341.8
2015/0223694 A1 8/2015 Funane et al.
(Continued)

FOREIGN PATENT DOCUMENTS

EP    3243444 A1    11/2017
JP    2007-111461 A    5/2007
(Continued)

OTHER PUBLICATIONS

Toru Yamada, et al., "Method for leveling the signal-to-noise ratio in multichannel functional near-infrared spectroscopy", Progress in Biomedical Optics and Imaging, SPIE—International Society for Optical Engineering, Bellingham, WA, U.S., vol. 10051, Feb. 8, 2017, pp. 1005118-1005118.

*Primary Examiner* — Jason M Ip
(74) *Attorney, Agent, or Firm* — Hoffmann & Baron, LLP (57) ABSTRACT

A device including a measuring unit having probes for emitting or detecting light with optical attenuators at points forming a regular triangle, and a control unit to: set transmittances of the attenuators so that an amount of light from the probes becomes a desired value; identify, among three channels, a first channel having a maximum light amount; perform detection in second and third channels between first and second probes of the first channel and a third probe; adjust transmittance of the attenuator of the first or the second probe of the channel having a smaller light amount so that light amounts in the second and the third channels become equal; adjust transmittance of the attenuator of the third probe so that the light amount of the second or the third (Continued)

channel becomes equal to the light amount of the first channel; and perform measurement with all transmittances after adjustments maintained.

10 Claims, 8 Drawing Sheets

(56) References Cited

U.S. PATENT DOCUMENTS

| | | |
|---|---|---|
| 2015/0238083 A1 | 8/2015 | Faubert et al. |
| 2018/0028098 A1 | 2/2018 | Yamada et al. |
| 2019/0290200 A1* | 9/2019 | Ishikawa ............ A61B 5/14553 |
| 2019/0380634 A1 | 12/2019 | Yamada |
| 2020/0029819 A1 | 1/2020 | Yamada |

FOREIGN PATENT DOCUMENTS

| | | |
|---|---|---|
| JP | 2012-5556 A | 1/2012 |
| JP | 2015-100410 A | 6/2015 |
| JP | 2018-29778 A | 3/2018 |
| JP | 2018-153533 A | 10/2018 |
| WO | WO 2012/005303 A1 | 1/2012 |
| WO | WO-2014034285 A1 * | 3/2014 ........... A61B 5/0042 |
| WO | WO 2016/111056 A1 | 7/2016 |
| WO | WO 2017/170804 A1 | 10/2017 |
| WO | WO 2018/190130 A1 | 10/2018 |

* cited by examiner

BRAIN FUNCTION MEASUREMENT DEVICE, BRAIN FUNCTION MEASUREMENT METHOD, AND PROBE

CROSS-REFERENCE TO RELATED APPLICATIONS

The present application is the U.S. National Phase of PCT/JP2019/050040, filed on Dec. 20, 2019, which claims priority to Japanese Patent Application No. 2019-034300, filed on Feb. 27, 2019, the entire contents of which are incorporated herein by reference.

BACKGROUND

Technical Field

The present invention relates to a device and a method for measuring brain functions.

Related Art

As a technique for measuring the functions of a brain, multichannel functional near-infrared spectroscopy (fNIRS) has been known. Various devices have so far been made with regard to the technique. For example, Patent Literature 1 discloses a technique by which, in order to increase measurement channel density and measurement time efficiency, probes each having irradiating and detecting roles that are switched temporally are disposed at the vertexes of a regular triangle, where the number of unitary units of the probes is increased as needed to arrange all of the probes.

CITATION LIST

Patent Literature

Patent Literature 1: JP 2015-100410 A

SUMMARY

Technical Problem

While the above-described probes are placed on the head of a subject, the signal-to-noise ratio (S/N ratio) necessarily varies significantly depending on the amount of hair at the measurement location. Thus, there has been the problem that it is difficult to compare data obtained at different measurement locations.

The present invention was made to solve the problem, and aims to provide a brain function measurement device, a brain function measurement method, and a probe for leveling, with respect to data obtained through measurement by functional near-infrared spectroscopy, a plurality of data items obtained at different measurement locations into data having a best S/N ratio in a simple manner so as to facilitate comparison of the plurality of data items.

Solution to Problem

In order to solve the problem, the present invention provides a brain function measurement device for performing measurement by functional near-infrared spectroscopy, including a measuring unit configured to perform optical emission or detection in an alternative manner and in which three probes, each of the three probes having an optical attenuator provided at a distal end thereof, are respectively disposed at the vertexes of a regular triangle, and a control unit configured to: initialize transmittances of all optical attenuators of the three probes so that an amount of light emitted from the three probes becomes a desired value; identify, among three channels to be measured by the three probes, a first channel having a maximum light amount obtained through the detection; perform the detection in second and third channels respectively positioned between first and second one of the three probes which are disposed at both ends of the first channel and a remaining third one of the three probes; adjust the transmittance of the optical attenuator provided for the first probe or the second probe disposed at one end of one of the second and the third channels in which a smaller light amount has been detected, so that the light amounts detected in the second and the third channels become equal; adjust the transmittance of the optical attenuator provided for the third one of the three probes so that the light amount detected in the second channel or the third channel becomes equal to the light amount detected in the first channel; and perform measurement by functional near-infrared spectroscopy in a state in which all adjusted transmittances are maintained.

Further, in order to solve the problem, the present invention provides a brain function measurement method of performing measurement by functional near-infrared spectroscopy using a measurement device which performs optical emission or detection in an alternative manner and in which three probes, each having an optical attenuator provided at a distal end thereof, are respectively disposed at the vertexes of a regular triangle, the method including: after the measurement device is placed on the head of a subject, initializing transmittances of all optical attenuators of the three probes so that an amount of light emitted from the three probes becomes a desired value; identifying, among three channels to be measured by the three probes, a first channel having a maximum light amount obtained through the detection; performing the detection in second and third channels respectively positioned between first and second ones of the three probes which are disposed at both ends of the first channel and a remaining third one of the probes; adjusting the transmittance of the optical attenuator provided for the first probe or the second probe disposed at one end of one of the second and the third channels in which a smaller light amount has been detected in the third step, so that the light amounts detected in the second and the third channels become equal; adjusting the transmittance of the optical attenuator provided for the third one of the three probes so that the light amount detected in the second channel or the third channel becomes equal to the light amount detected in the first channel; and performing measurement by functional near-infrared spectroscopy in a state in which all adjusted transmittances are maintained.

Further, in order to solve the problem, the present invention provides a probe with which a brain function measurement device for performing measurement by functional near-infrared spectroscopy is equipped, the probe including: an optical attenuator provided at a distal end; a light source configured to emit light from the distal end through the optical attenuator; and a detector configured to detect light received at the distal end through the optical attenuator.

Advantageous Effects of Invention

According to the present invention, it is possible to provide a brain function measurement device, a brain function measurement method, and a probe for leveling, with respect to data obtained through measurement by functional near-infrared spectroscopy, a plurality of data items obtained at different measurement locations into data having a best S/N ratio in a simple manner so as to facilitate comparison of the plurality of data items.

DETAILED DESCRIPTION

In the following, embodiments of the present invention will be described with reference to the drawings. Throughout the drawings, similar reference signs designate similar or equivalent portions.

Figure 1:
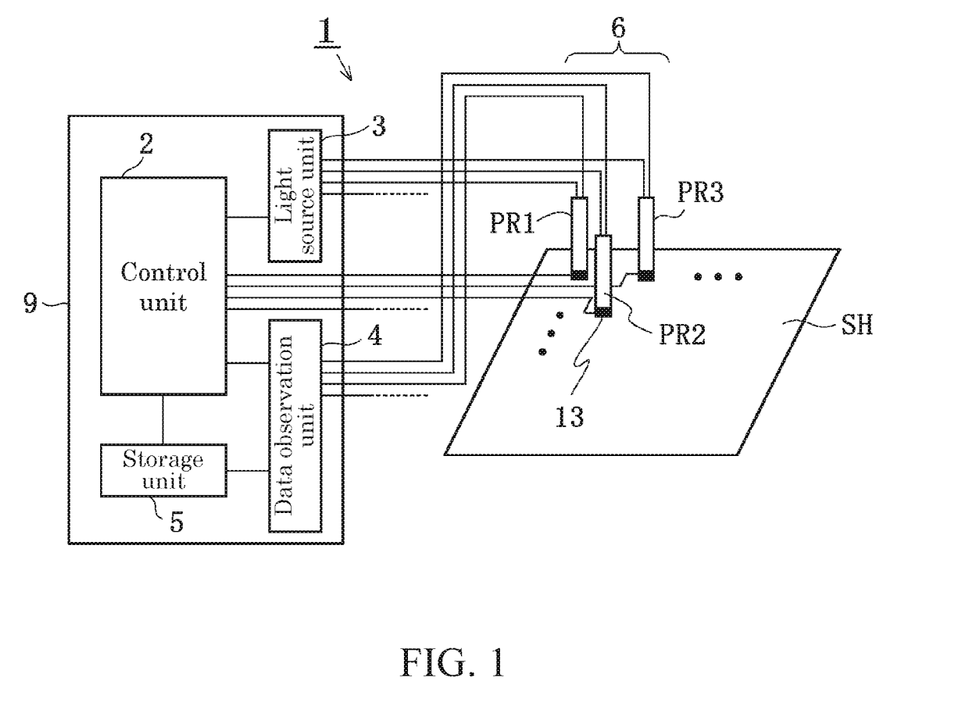
FIG. 1 illustrates an overall configuration of a brain function measurement device 1 according to an embodiment of the present invention.

FIG. 1 illustrates an overall configuration of a brain function measurement device 1 according to an embodiment of the present invention. As illustrated in FIG. 1, the brain function measurement device 1 according to the embodiment of the present invention is a device for performing measurement by functional near-infrared spectroscopy, and is provided with a measuring unit 6 placed on the head SH of a subject, and a brain function measurement unit 9 connected to the measuring unit 6.

The measuring unit 6 includes at least three probes PR1 to PR3, each having an optical attenuator 13 at the distal end thereof, and respectively disposed at the vertexes of a regular triangle to perform optical emission or detection in an alternative manner.

As the optical attenuator 13, it may be preferable to use an electrochromic element disclosed in WO 2018/025939, for example.

In FIG. 1, the configuration of the measuring unit 6 is illustrated in a simplified manner. A concrete configuration of the measuring unit 6 is described in detail below.

Further, in the following, an example in which the measuring unit 6 is composed of the three probes PR1 to PR3 will be described, followed by the description of an example in which the measuring unit 6 is configured of four or more probes.

The brain function measurement unit 9 includes: a light source unit 3 which is connected to the probes PR1 to PR3 and supplies light to each of the probes PR1 to PR3; a data observation unit 4 which is connected to the probes PR1 to PR3 and observes amounts of light detected by the probes PR1 to PR3; a storage unit 5 which is connected to the data observation unit 4 and stores light amount data obtained by the data observation unit 4; and a control unit 2 which is connected to the light source unit 3, the data observation unit 4, the storage unit 5, and the optical attenuator 13. The control unit 2 implements the alternative operation of each of the probes PR1 to PR3 and causes the light amount data to be stored in the storage unit 5.

The control unit 2 achieves the alternative operation through the following control. The control unit 2 designates a probe for emitting light and thereby causes the light source unit 3 to supply light to the probe, and designates a probe for detecting light and thereby causes the data observation unit 4 to observe the amount of light detected by the probe.

The control unit 2 also controls the attenuation rate of the optical attenuator 13 provided at the distal end of each of the probes PR1 to PR3, as will be described in detail below.

Figure 2:
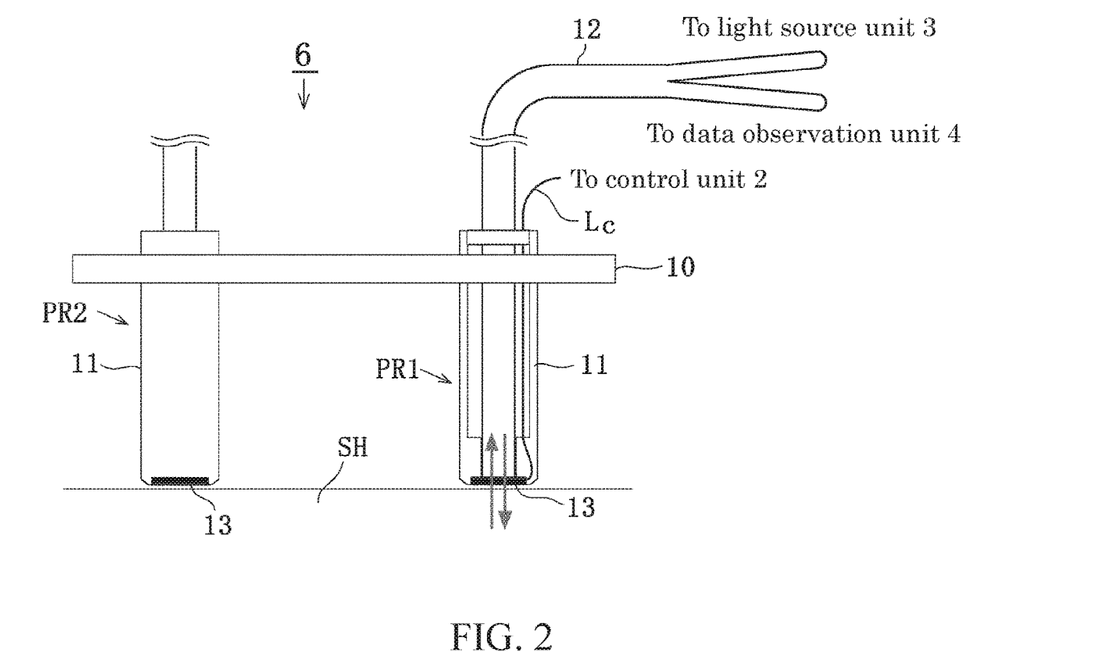
FIG. 2 illustrates a configuration example of a measuring unit 6 illustrated in FIG. 1.

FIG. 2 illustrates a configuration example of the measuring unit 6 illustrated in FIG. 1. FIG. 2 illustrates a cross sectional structure of the measuring unit 6 when viewed laterally, where the probe PR3 is omitted. The arrows shown at the distal end of the probe PR1 indicate the directions in which light travels.

As illustrated in FIG. 2, the probes PR1 to PR3 are supported by a holder 10. Each of the probes PR1 to PR3 is configured of a housing 11 in which there is housed a bifurcated optical fiber 12 having the optical attenuator 13 attached to the distal end thereof.

The bifurcated optical fiber 12 bifurcates into one part for leading light supplied from the light source unit 3 to the distal end, and the other part for leading the light detected at the distal end through the optical attenuator 13 to the data observation unit 4. A control signal line Lc which is used by the control unit 2 to control the optical attenuator 13 is housed in the housing 11.

Figure 3:
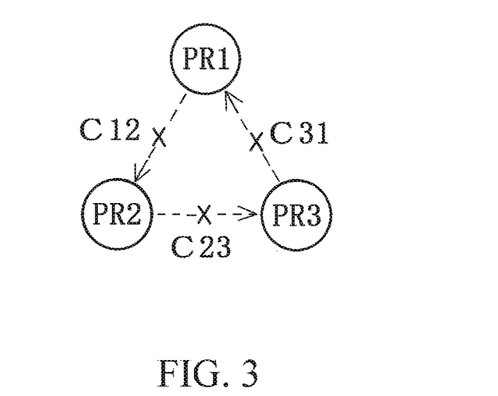
FIG. 3 illustrates a planar arrangement of probes PR1 to PR3 illustrated in FIG. 1.

FIG. 3 illustrates a planar arrangement of the probes PR1 to PR3 illustrated in FIG. 1. As illustrated in FIG. 3, the three probes PR1 to PR3 are disposed at the vertexes of a regular triangle (hereafter referred to as a "three-point multidirectional arrangement".

In a measurement channel C12, light emitted from the light probe PR1 in the direction of arrow shown in FIG. 3 is detected by the probe PR2, whereby an observation light amount Jc12 can be obtained. In a measurement channel C23, light emitted from the probe PR2 in the direction of arrow is detected by the probe PR3, whereby an observation light amount Jc23 can be obtained. Similarly, in a measurement channel C31, light emitted from the probe PR3 in the direction of arrow is detected by the probe PR1, whereby an observation light amount Jc31 can be obtained.

The observation light amounts are each the product of a light amount I outputted from the distal end of the bifurcated optical fiber 12, a transmittance ai of the optical attenuator 13 attached to the distal end of an emitting-side probe, an optical transmittance ri between the probe and the scalp of the subject, a tissue transmittance R, an optical transmittance rj between a detecting-side probe and the scalp of the subject, and a transmittance aj of the optical attenuator 13 attached to the distal end of the probe.

Herein, the product (I×ai×ri) is referred to as an effective incident light amount, and the product (rj×aj) is referred to as an effective detection efficiency. The effective incident light amount and the effective detection efficiency vary depending on the amount of hair that exists between each probe and the scalp of the subject. Accordingly, because each probe only provides either an emitting function or a detecting function at a particular point in time, the positions of the probe that indicates a maximum effective incident light amount and the probe that indicates a maximum effective detection efficiency are necessarily different, and their values are also different.

Accordingly, if leveling is achieved by comparing the maximum effective incident light amount and the maximum effective detection efficiency and matching the effective incident light amounts or the effective detection efficiencies of all of the measurement channels to the greater value, greater observation light amounts can be obtained in all of the measurement channels. As a result, data having a better S/N ratio can be obtained.

Each of the probes PR1 to PR3 illustrated in FIG. 1 has the functions of an emitting probe and a detecting probe. Thus, by attaching a single optical attenuator to the distal end of each of the probes PR1 to PR3, it is possible to match the optical transmittance during emission with the optical transmittance during detection in each of the probes PR1 to PR3. Thus, the probe indicating a maximum effective incident light amount matches with the probe indicating a maximum effective detection efficiency at all times, and the optical transmittance of the probe can be uniquely obtained. Accordingly, by performing noise leveling when performing measurement by functional near-infrared spectroscopy under the three-point multidirectional arrangement described above, it is possible to cause a plurality of data items obtained at different measurement locations to necessarily be leveled to have the best signal-to-noise ratio (S/N ratio).

Figure 4:
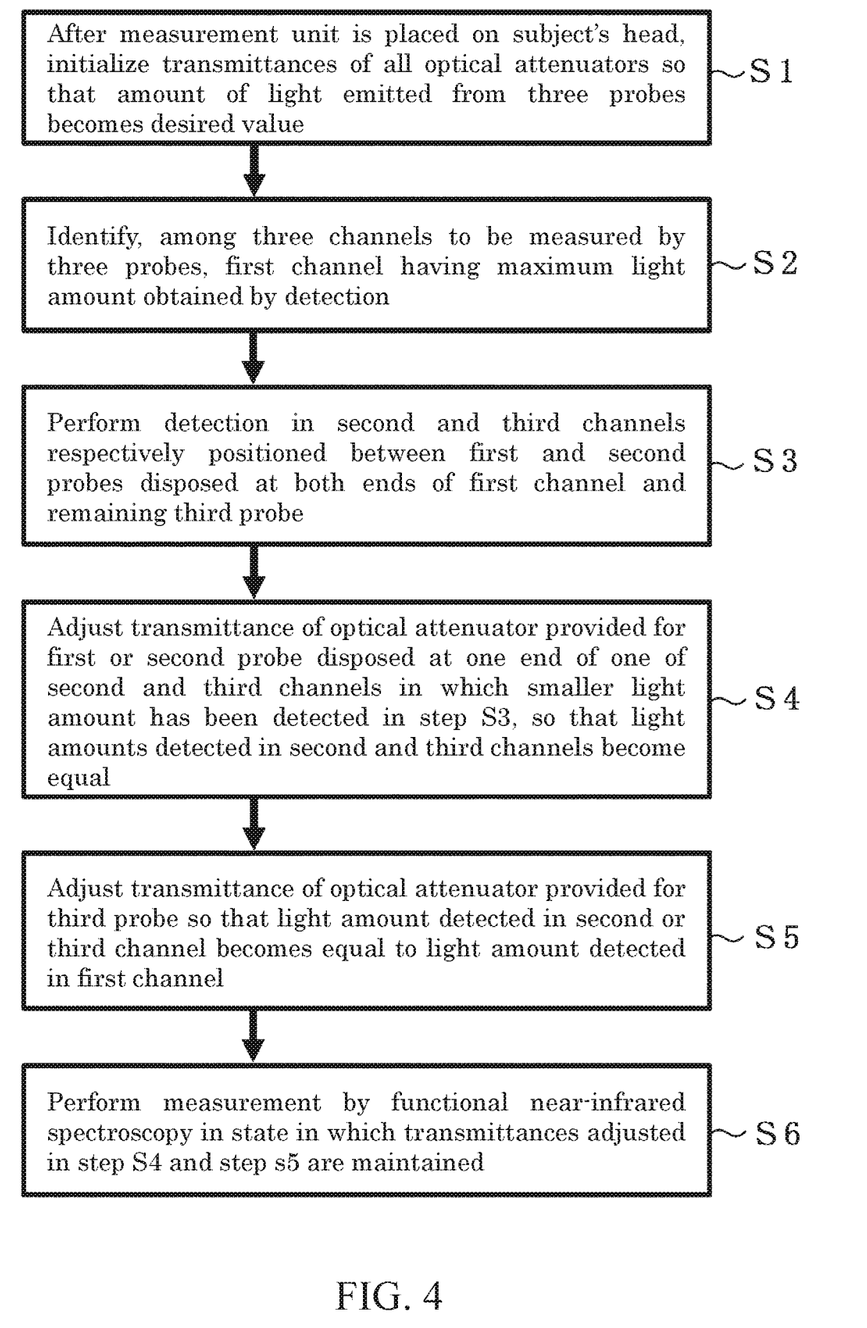
FIG. 4 is a first flowchart of a brain function measurement method according to an embodiment of the present invention.

FIG. 4 is a first flowchart of a brain function measurement method according to an embodiment of the present invention. In the following, with reference to FIG. 4, implementation of the brain function measurement method using the brain function measurement device 1 illustrated in FIG. 1 will be described. Needless to say, the present method is not limited to the case in which the brain function measurement device 1 is used, but is broadly applicable.

Referring to FIG. 4, the brain function measurement method according to the embodiment of the present invention is a method for performing measurement by functional near-infrared spectroscopy. In step S1, after the measuring unit 6 is placed on or attached to the head of a subject, the control unit 2 initializes the transmittances of all the optical attenuators 13 so that the amount of light emitted from the three probes PR1 to PR3 becomes a value desired by the user, such as a maximum emitted light amount that is considered safe with respect to the subject, for example.

In an example, the desired value may be stored in the storage unit 5 in advance, so that the control unit 2 can automatically read the desired value stored in the storage unit 5 for the initializing. Alternatively, the desired value may be supplied in each case by the user to the control unit 2, via an input unit (not illustrated).

In step S2, the control unit 2, with reference to the light amount data stored in the storage unit 5, identifies a measurement channel having a maximum observation light amount. In the following, a first measurement channel having the maximum observation light amount is the measurement channel C12. As illustrated in FIG. 3, first and second probes disposed on both ends of the first measurement channel are the probes PR1, PR2, and a third probe adjacent thereto is the probe PR3. Second and third measurement channels respectively positioned between the probes PR1, PR2 and the remaining probe PR3 are the measurement channels C31, C23.

In step S3, the control unit 2 performs the detection in the second and the third measurement channels C31, C23 respectively positioned between the first and second probes PR1, PR2, which are disposed on both ends of the first measurement channel, i.e., the measurement channel C12, and the remaining third probe PR3.

In step S4, the control unit 2 adjusts the transmittance of the optical attenuator 13 provided for the first or the second probe PR1, PR2 that is disposed at one end of one of the second and the third measurement channels C31, C23 in which a smaller light amount has been detected in step S3, so that the light amounts detected in the third and the second measurement channels C23, C31 become equal.

In step S5, the control unit 2 adjusts the transmittance of the optical attenuator 13 provided for the third probe PR3 so that the light amounts detected in the first and the second measurement channels C12, C31, or the light amounts detected in the first and the third measurement channels C12, C23 become equal.

In step S6, the brain function measurement device 1 performs measurement by functional near-infrared spectroscopy in a state in which the transmittances adjusted in step S4 and step S5 are maintained.

Figure 5:
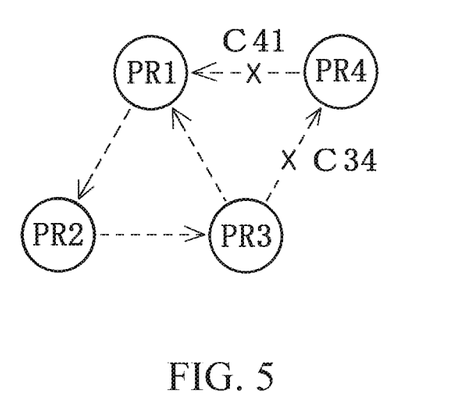
FIG. 5 is a diagram for describing the brain function measurement method in an example in which the measuring unit 6 illustrated in FIG. 1 is composed of four probes.

FIG. 5 is a diagram for describing the brain function measurement method in an example in which the measuring unit 6 illustrated in FIG. 1 is composed of four probes PR1 to PR4. As illustrated in FIG. 5, the four probes PR1 to PR4 are disposed in the three-point multidirectional arrangement. Specifically, the probes PR1 to PR3 are disposed similarly to FIG. 3, and the probe PR4 having the same configuration as that of the probes PR1 to PR3 is disposed at a fourth vertex of another regular triangle of which one side is provided by one side of the regular triangle formed by the positions of the probes PR1 to PR3.

Figure 6:
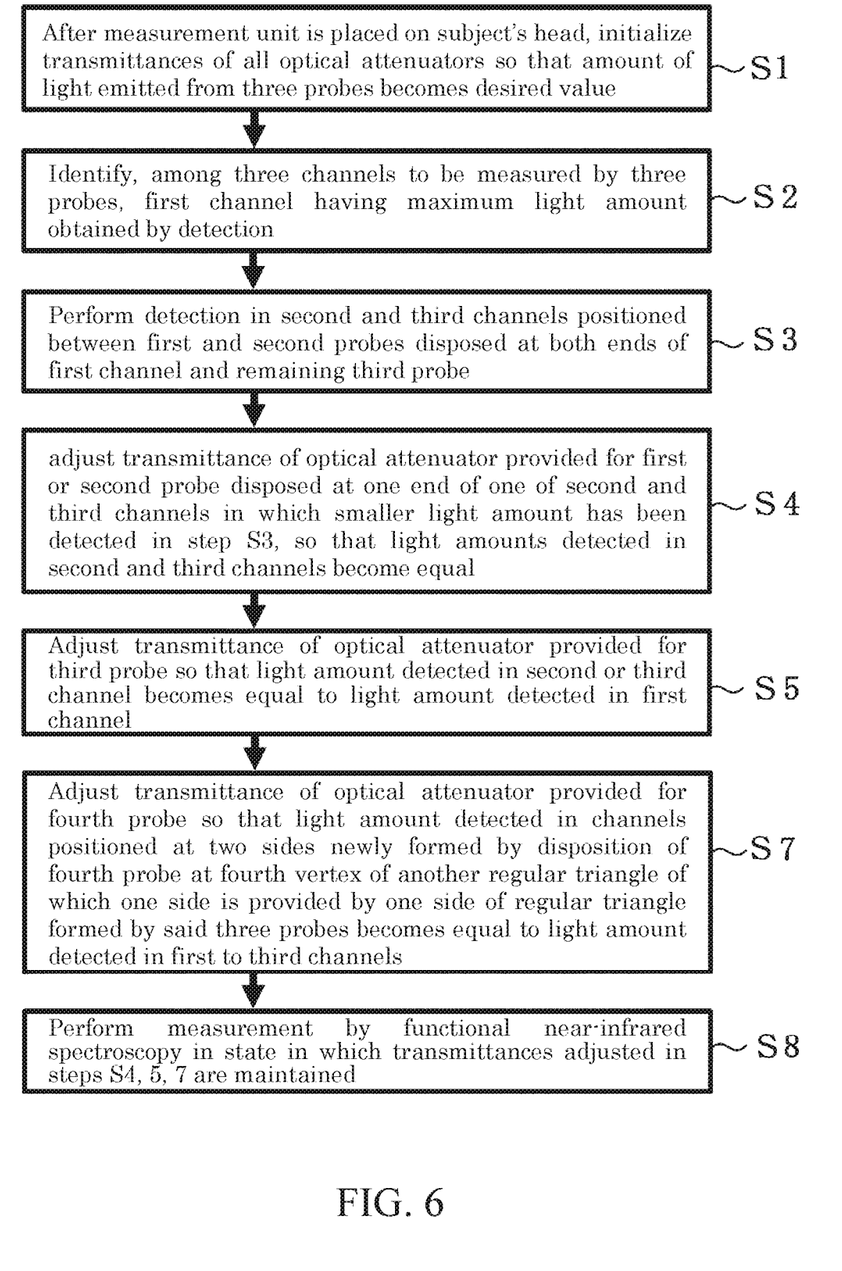
FIG. 6 is a second flowchart of the brain function measurement method according to the embodiment of the present invention.

In this case, referring to FIG. 6, the control unit 2, following the steps S1 to S5, adjusts the transmittance of the optical attenuator 13 provided for the probe PR4 so that the light amount detected in measurement channels C34, C41 positioned at the two sides newly formed by the disposition of the probe PR4 becomes equal to the light amount detected in the first to third measurement channels C12, C23, C31 (step S7).

Then, the brain function measurement device 1 performs (step S8) the measurement by functional near-infrared spectroscopy in step S6 in a state in which the transmittance adjusted in step S7 is also maintained, i.e., in a state in which the transmittances adjusted in steps S4, S5, S7 are maintained.

Figure 7:
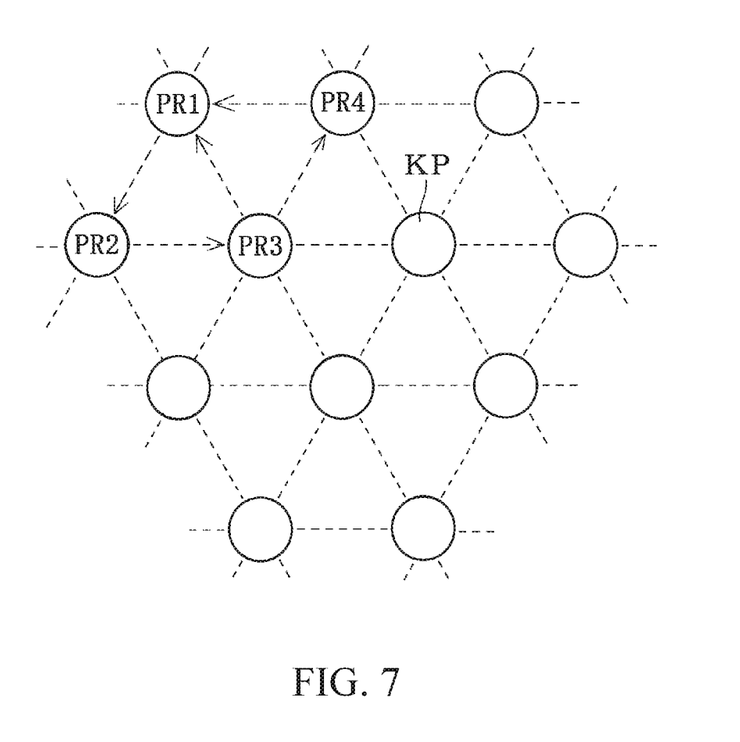
FIG. 7 is a diagram for describing the brain function measurement method in an example in which the measuring unit 6 illustrated in FIG. 1 is composed of five or more probes.

FIG. 7 is a diagram for describing the brain function measurement method in an example in which the measuring unit 6 illustrated in FIG. 1 is composed of five or more probes. As illustrated in FIG. 7, the five or more probes are disposed in the three-point multidirectional arrangement. Specifically, the respective probes are disposed over lattice points KP forming the regular triangles. Such arrangement enables maximization of the measurement channel space density.

In this case, the control unit 2 further repeats an adjustment similar to that of step S7 for each of the three probes of the regular triangle that is newly formed.

The control unit 2 may cause the transmittances of the optical attenuators 13 that have been adjusted as described above to be stored in the storage unit 5. When measurement is performed on a different date/time or for a different subject, the transmittances of the optical attenuators 13 may be set to the stored values. In this way, it becomes possible to perform measurement under the same condition also in the above cases, so that a plurality of data items acquired in the above cases can be easily compared with each other.

Figure 8:
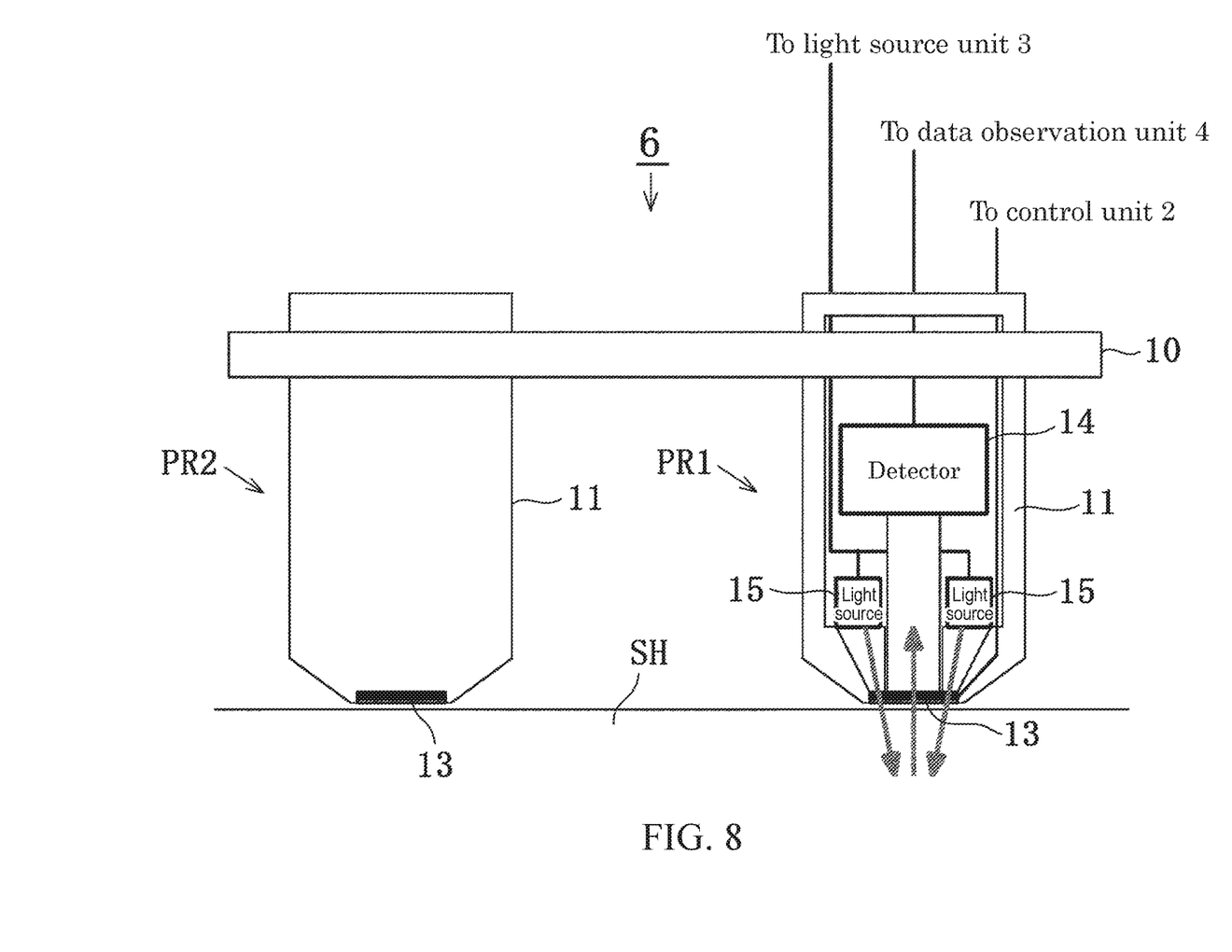
FIG. 8 illustrates another configuration example of the measuring unit 6 illustrated in FIG. 1.

The measuring unit 6 illustrated in FIG. 1 is not limited to the configuration illustrated in FIG. 2, and may have a configuration illustrated in FIG. 8. FIG. 8 illustrates a cross sectional structure of the other configuration of the measuring unit 6 when viewed laterally, where the probe PR3 is omitted. The arrows shown at the distal end of the probe PR1 indicate directions of travel of light.

The measuring unit 6 illustrated in FIG. 8, similarly to the measuring unit 6 illustrated in FIG. 2, includes the housing 11 supported by the holder 10. The housing 11 incorporates the optical attenuator 13 disposed at the distal end, light sources 15 for emitting light from the distal end through the optical attenuator 13, and a detector 14 for performing the detection.

The optical attenuator 13 is connected to the control unit 2, and the transmittance is adjusted in accordance with a control signal supplied from the control unit 2. The light sources 15 are connected to the light source unit 3, and the on/off of the light sources 15 is switched in accordance with a control signal supplied from the light source unit 3. The detector 14 is connected to the data observation unit 4, and the on/off of the detector 14 is switched in accordance with a control signal supplied from the data observation unit 4.

Figure 9:
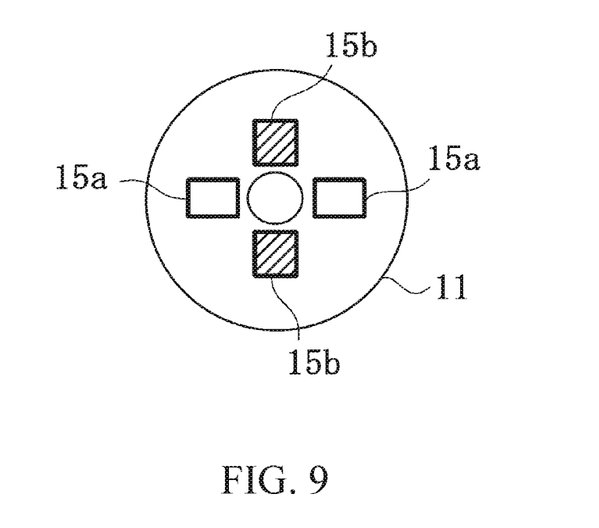
FIG. 9 is a planar configuration diagram illustrating a first arrangement example of light sources 15 illustrated in FIG. 8.
Figure 10:
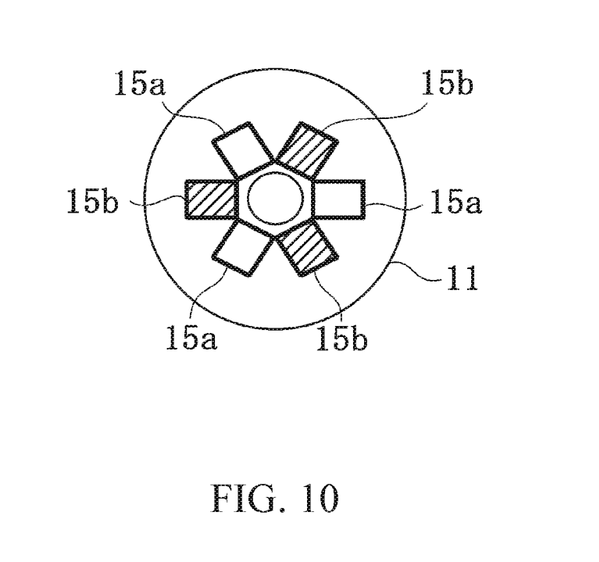
FIG. 10 is a planar configuration diagram illustrating a second arrangement example of the light sources 15 illustrated in FIG. 8.

FIG. 9 is a planar configuration diagram illustrating a first arrangement example of the light sources 15 illustrated in FIG. 8. As illustrated in FIG. 9, in the first arrangement example, two light sources 15a emitting light having a first wavelength and two light sources 15b emitting light having a second wavelength are respectively disposed at positions which are point-symmetric with respect to the central axis of the housing 11. The number of the light sources 15a, 15b is not limited to two each and may be three each, for example, in which case the light sources may be disposed as illustrated in FIG. 10.

As described above, according to the brain function measurement device, the brain function measurement method, and the probe according to the embodiments of the present invention, it is possible to level, with respect to data obtained through measurement by functional near-infrared spectroscopy, a plurality of data items obtained at different measurement locations into data having the best S/N ratio in a simple manner so as to facilitate comparison of the plurality of data items.

REFERENCE SIGNS LIST

1 Brain function measurement device
2 Control unit
3 Light source unit
4 Data observation unit
6 Measuring unit
11 Housing
12 Bifurcated optical fiber
13 Optical attenuator
14 Detector
15, 15a, 15b Light source
PR1-PR4 Probe

The invention claimed is:

1. A brain function measurement device fib performing measurement by functional near-infrared spectroscopy, the brain function measurement device comprising:

a measurement unit configured to perform optical emission and alternatively optical detection, the measurement unit comprising three probes that include a first probe, a second probe, and a third probe, each of the three probes having an optical attenuator provided at a distal end thereof, the three probes supported by a holder and respectively disposed at vertexes of a first regular triangle; and a control unit configured to:
initialize transmittances of all optical attenuators of the three probes so that an amount of light emitted from the three probes becomes a desired value, the desired value being read from a storage unit or supplied from an input unit;
identify, among three channels to be measured by the three probes, a first channel having a maximum light amount Obtained through detection performed in advance;
perform detection in a second channel and a third channel respectively positioned between the first probe and the second probe which are disposed at both ends of the first channel and the third probe to detect which of the second channel and the third channel has a smaller light amount;
adjust transmittance of the optical attenuator provided for the first probe or the second probe disposed at one end of one of the second channel and the third channel in which the smaller light amount has been detected, so that light amounts detected in the second channel and the third channel become equal;
adjust transmittance of the optical attenuator provided for the third probe so that a light amount detected in the second channel or the third channel becomes equal to a light amount detected in the first channel; and
perform measurement by functional near-infrared spectroscopy in a state in which all adjusted transmittances are maintained.

2. The brain function measurement device according to claim 1, wherein:
the measurement unit further includes a fourth probe having same configuration as the first probe, the second probe, and the third probe of the three probes, the fourth probe disposed at a fourth vertex of a second regular triangle of which one side is provided by one side of the first regular triangle; and
the control unit is further configured to adjust transmittance of an optical attenuator provided for the fourth probe so that a light amount detected in channels positioned at two sides of the second regular triangle newly formed by the disposition of the fourth probe becomes equal to a light amount detected in the three channels of the first regular triangle.

3. The brain function measurement device according to claim 2, wherein:
the measurement unit includes five or more probes respectively disposed over lattice points of a plurality of regular triangles; and
the control unit is further configured to repeat adjustments for three probes of each regular triangle that is newly formed in the plurality of regular triangles.

4. The brain function measurement device according to claim 1, the device further comprising:
a light source unit configured to supply the light to the three probes; and
an observation unit configured to observe an amount of light detected by the three probes, wherein each of the three probes includes a bifurcated optical fiber which leads the light supplied from the light source unit to the distal end, and leads the light detected at the distal end through the optical attenuator to the observation unit.

5. The brain function measurement device according to claim 1, wherein each of the three probes incorporates:
a light source configured to emit the light from the distal end through the optical attenuator; and
a detector configured to perform the detection.

6. The brain function measurement device according to claim 1, further comprising a storage unit configured to store the adjusted transmittances as adjusted by the control unit.

7. A brain function measurement method of performing measurement by functional near-infrared spectroscopy using a measurement device which performs optical emission and alternatively optical detection, the measurement device comprising three probes that include a first probe, a second probe, and a third probe, each of the three probes having an optical attenuator provided at a distal end thereof, the three probes supported by a holder and respectively disposed at vertexes of a first regular triangle, the method comprising:
after the measurement device is placed on the head of a subject, initializing transmittances of all optical attenuators of the three probes so that an amount of light emitted from the three probes becomes a desired value, the desired value being read from a storage unit or supplied from an input unit;
identifying, among three channels to be measured by the three probes, a first channel having a maximum light amount obtained through detection performed in advance;
performing detection in a second channel and a third channel respectively positioned between the first probe and the second probe which are disposed at both ends of the first channel and the third probe to detect which of the second channel and the third channel has a smaller light amount:
adjusting the transmittance of the optical attenuator provided for the first probe or the second probe disposed at one end of one of the second channel and the third channel in which the smaller light amount has been detected, so that light amounts detected in the second channel and the third channel become equal;
adjusting the transmittance of the optical attenuator provided for the third probe so that a light amount detected in the second channel or the third channel becomes equal to a light amount detected in the first channel; and
performing measurement by functional near-infrared spectroscopy in a state in which all adjusted transmittances are maintained.

8. The brain function measurement method according to claim 7, wherein the measurement device further includes a fourth probe having same configuration as the first probe, the second probe, and the third probe of the three probes, the fourth probe disposed at a fourth vertex of a second regular triangle of which one side is provided by one side of the first regular triangle, the method further comprising:
adjusting transmittance of an optical attenuator provided for the fourth probe so that a light amount detected in channels positioned at two sides of the second regular triangle newly formed by the disposition of the fourth probe becomes equal to a light amount detected in the three channels of the first rectangular triangle,
wherein the performing measurement is performed in a state in which the transmittance adjusted for the fourth probe is also maintained.

9. The brain function measurement method according to claim 8, wherein the measurement device includes five or more probes respectively disposed over lattice points of a plurality of regular triangles, the method further comprising:
repeating adjustments for three probes of each regular triangle that is newly formed in the plurality of regular triangles,
wherein the performing measurement is performed in a state in which the transmittance adjusted is also maintained for each of the three probes in each regular triangle that is newly formed.

10. The brain function measurement method according to claim 7, the method further comprising:
setting the transmittances of optical attenuators to the transmittances adjusted for the first probe or the second probe, and for the third probe; and
performing the measurement on a different date/time or for a different subject.

* * * * *